United States Patent [19]

Hiraga et al.

[11] 4,389,483

[45] Jun. 21, 1983

[54] METHOD FOR PRODUCING L-GLUTAMIC ACID BY FERMENTATION

[75] Inventors: Hirofumi Hiraga, Yokohama; Minoru Yoshimura, Kawasaki; Shigeho Ikeda; Hiroe Yoshii, both of Yokohama, all of Japan

[73] Assignee: Ajinomoto Company Incorporated, Tokyo, Japan

[21] Appl. No.: 331,758

[22] Filed: Dec. 17, 1981

[30] Foreign Application Priority Data

Dec. 29, 1980 [JP] Japan .................................. 55-185678

[51] Int. Cl.³ ...................... C12P 13/14; C12P 13/18; C12R 1/13; C12R 1/15
[52] U.S. Cl. .................................. 435/110; 435/111; 435/840; 435/843
[58] Field of Search .............................. 435/110–112, 435/840, 843

[56] References Cited

U.S. PATENT DOCUMENTS

| | | | |
|---|---|---|---|
| 3,440,141 | 4/1969 | Douros et al. | 435/110 |
| 3,498,883 | 3/1970 | Iguchi et al. | 435/110 X |
| 3,511,752 | 5/1970 | Tanaka et al. | 435/110 X |
| 3,764,473 | 10/1973 | Tanaka et al. | 435/110 X |
| 3,971,701 | 7/1976 | Takinami et al. | 435/111 |
| 4,334,020 | 6/1982 | Nakazawa et al. | 435/110 |
| 4,347,317 | 8/1982 | Yoshimura et al. | 435/110 |

FOREIGN PATENT DOCUMENTS 56-140895 11/1981 Japan .................................. 435/110

*Primary Examiner*—Lionel M. Shapiro
*Attorney, Agent, or Firm*—Oblon, Fisher, Spivak, McClelland & Maier

[57] ABSTRACT

A method for producing L-glutamic acid by fermentation which comprises culturing aerobically in a culture medium a mutant of the genus of Brevibacterium or Corynebaterium which is resistant to Decoyinine or Tubercidin and capable of producing L-glutamic acid, and recovering the L-glutamic acid accumulated in the culture medium.

3 Claims, No Drawings

METHOD FOR PRODUCING L-GLUTAMIC ACID BY FERMENTATION

The present invention relates to a method for producing L-glutamic acid by fermentation.

L-glutamic acid, in the form of the monosodium salt, has been used as a seasoning and has been produced by a fermentation process in which wild strains or artificial mutants of L-glutamic acid producing bacteria, especially of the genus Brevibacterium or Corynebacterium, are used.

Up to the present, various artificial mutants of the genus Brevibacterium or Corynebacterium have been known which produce L-glutamic acid. Examples of such artificial mutants are mutants which require L-Arginine, L-histidine, pyrimidine, hypoxanthine, glycerol, a chemical compound containing the disulfide linkage, or an unsaturated fatty acid such as oleic acid (Japanese Published Examined Patent Application No. 507/1667, 508/1967, 509/1667, 27390/1970, 27391/1970, 19632/1975, 33997/1976, 2998/1977, 6233/1978, 6234/1978, 8798/1978); mutants resistant to chloramphenicol, streptomycin, chlortetracycline, S-(2-aminoethyl)-cystein, monofluoroacetic acid, fluorocitric acid, ketomalonic acid, α-amino-β-hydroxyvaleric acid, DL-threonine hydroxamate, 2-amino-3-phosphopropionic acid, 5-aminolevulinic acid, glutamic acid-analogue, benzopyrone, naphthoquinone, 2,6-pyridine-dicarboxylic acid or inhibitors of the respiratory system such as malonic acid, $NaN_3$ KCN, sodium arsenite 2,4-dinitrophenol, hydroxyamine and guanidine, (Japanese Published Unexamined Patent Application Nos. 4398/1966, 126877/1975, 38088/1977, 89085/1979, 21763/1980, 21764/1980, 124492/1980, 1889/1981, 35981/1981, 39778/1981, 48890/1981); mutants sensitive to N-palmitoyl glutamic acid, lysozyme, or to a temperature more than 34° C. (Japanese Published Unexamined Patent Application Nos. 64486/1975, 32193/1978, 66687/1977, 122794/1979, 114293/1980) and mutant having reduced pyruvic acid dehydrogenase activity (Japanese Published Unexamined Patent Application No. 21762/1980).

It has now been found that the productivity of L-glutamic acid can be increased when resistance to Decoyinine or Tubercidin is imparted to known L-glutamic acid producing microorganisms.

The microorganisms employed according to the present invention are mutants which belong to the genus Brevibacterium or Corynebacterium, are resistant to Decoyinine or Tubercidin and have an ability to produce L-glutamic acid.

Exemplary specimens of the mutants of the present invention are:

| | |
|---|---|
| Brevibacterium lactofermentum | AJ 11638 FERM-P 5812 FERM BP-74 (Dec$^r$) |
| Brevibacterium lactofermentum | AJ 11637 FERM-P 5811 FERM BP-73 (Tub$^r$) |
| Corynebacterium glutamicum | AJ 11645 FERM P-5819 FERM BP-75 (Dec$^r$) |

(Dec$^r$): resistance to Decoyinine
(Tub$^r$): resistance to Tubercidin

The mutants identified above by FERM-BP numbers were originally deposited with the FERM-P numbers on Dec. 22, 1980 at the Fermentation Research Institute, Agency of Industrial Science and Technology, Ministry of International Trade and Industry (FRI), 1-3, Higashi 1-chome, Yatabe-machi, Tsukuba-gun, Ibaragi-ken 305, Japan. The deposits have been converted to deposits under the Budapest Treaty on Dec. 9, 1981 with FRI which has acquired the status of an International Depository Authority as of May 1, 1981.

The mutants as stated above can be induced from parent strains of the genus Brevibacterium or Corynebacterium by conventional methods.

The first step of the induction process is to mutate parent strains with a suitable chemical mutagen such as N-methyl-N'-nitro-N-nitro-soguanidine (hereinafter referred to as NG) and nitrous acid or with irradiation of ultraviolet light.

The second step is to select a mutant resistant to antibiotics by collecting the colonies which grow on plates of nutrient agar medium containing an amount of the antibiotic which inhibits the growth of the parent strain. Finally, the mutants are envaluated for L-glutamic acid productivity by a standard method. Decoyinine (Angustmycin) and Tubercidin which are utilized in the present invention are antibiotics which are related to Purine and Pyrimidine.

The mutants of the present invention resistant to Decoyinine and Tubercidin are very resistant to other antibiotics related to Purine and Pyrimidine such as Psicofuranine (Angustmycin C), Formycin, Toyocamycin, Cordice and Sangivamycin, and the mutants of the present invention can also be induced by using these antibiotics instead of Decoyinine and Tubercidin.

As the parent strain of the genus Brevibacterium or Corynebacterium; any wild strain capable of producing L-glutamic acid can be employed. The preferred wild strains are coryne-form glutamic acid producing bacteria and suitable examples include:

| | |
|---|---|
| Brevibacterium lactofermentum | ATCC 13869 |
| Brevibacterium flavum | ATCC 14067 |
| Brevibacterium divaricatum | ATCC 14020 |
| Brevibacterium saccharoliticum | ATCC 14066 |
| Corynebacterium glutamicum | ATCC 13032 |
| Corynebacterium acetoacidophilum | ATCC 13870 |

Another type of suitable parent strain is that from which mutants of the genus Brevibacterium or Corynebacterium can be induced from wild strains as stated above and which have biological characteristics known to be effective for the production of L-glutamic acid such as resistance to fluoro-malonic acid, fluoro-citric acid, keto-malonic acid and 2,6-pyridine dicarboxylic acid. Those which are sensitive to lysozyme and N-palmitoyl-glutamate are preferably used.

These characteristics, useful for the production of L-glutamic acid, can be imparted prior to or after imparting antibiotic resistance to the wild strains.

The method by which the mutants of the present invention are induced and the degree of resistance to the antibiotics are shown in Experiments 1 and 2.

EXPERIMENT 1

*Brevibacterium lactofermentum* ATCC 13869, which grows on a slant of bouillon agar medium, were scraped together and suspended in sterilized water containing 250 mcg/ml NG and the suspension was allowed to stand at 30° C. for 30 minutes. The microbial cells thus treated were washed with phosphate buffer solution and then inoculated on the agar plates of a GM medium of which the composition is given in Table 1 further containing 200/ml Decoyinine.

TABLE 1

| Composition of GM medium | | | |
|---|---|---|---|
| Component | Conc. | Component | Conc. |
| Glucose | 0.5 g/dl | $CaCl_2$ | 0.1 mg/dl |
| Ammonium sulfate | 0.15 g/dl | $MnCl_2\ 4\ H_2O$ | 0.36 mg/dl |
| Urea | 0.15 g/dl | $Na_2B_4O_7\ 10\ H_2O$ | 0.44 mg/dl |
| $K_2HPO_4$ | 0.1 g/dl | $CuSO_4\ 5\ H_2O$ | 1.95 mg/dl |
| $KH_2PO_4$ | 0.3 g/dl | $ZnSO_4\ 7\ H_2O$ | 44 mg/dl |
| $Mg\ SO_4\ 7\ H_2O$ | 0.01 g/dl | Biotin | 3 µg/ml |
| $FeCl_3\ 6\ H_2O$ | 4.85 g/dl | Thiamine HCl | 10 µg/ml |
| $(NH_4)Mo_7O_{24}\ 4\ H_2O$ | 0.18 g/dl | | |

The plates were then incubated at 30° C. for 2 to 4 days until colonies turned up on the plates. The colonies were picked-up as the Decoyinine-resistant mutants and were evaluated for productivity of L-glutamic acid according to a standard method.

It was found that the mutants having a higher productivity of L-glutamic acid than the parent strain were obtained with high frequency.

From among these mutants, B. lactofermentum AJ 11638 FERM BP, which can produce more L-glutamic acid than any other mutant, was selected. The mutants of the present invention resistant to Tubercidine were obtained in a manner similar to that above.

EXPERIMENT 2

Four ml portions of an aqueous G M medium in Table 1 further containing 1–3 mg/ml Antibiotics were poured into small-size test tubes and heated for sterilization.

Each test strain was washed with the G M medium and suspended in a G M medium to prepare a cell suspension of which the optical density at 26 times dilution at 562 nm was 0.1. A 0.1 ml amount of the cell suspension (0.1 ml) was then transferred into each batch of G M medium placed in a test tube. Cultivation was carried out at 30° C. for 24 hours with shaking. After the cultivation, the degree of growth of each strain was determined by measuring the optical density at 562 nm at 26 times dilution of the resulting culture broth. The results obtained are shown in Table 2.

In Table 2, the degree of resistance to the antibiotics are relative values of the growth of the colonies versus a control.

The mutants are cultured aerobically in a conventional culture medium containing carbon sources, nitrogen sources and inorganic ions, and minor nutrients when required. Suitable carbon sources preferably include saccharides such as glucose, sucrose, molasses and hydrolyzed starch, organic acids such as acetic acid and propionic acid and alcohols such as ethanol suitable nitrogen sources include, for example, ammonium sulfate, gaseous ammonia and urea. Inorganic ions such as, $K^+$, $Na^+$, $Ca^{++}$, $Fe^{++}$, $Mn^{++}$, $Mg^{++}$, $Zn^{++}$, $SO_4^{--}$, $Cl^-$ and $PO_4^{--}$ are added to the culture medium as required.

When a carbon source which does not contain biotin, such as hydrolyzed starch is employed, biotin is added to the culture medium and its concentration in the medium has to be controlled to an amount less than the proper amount for the growth of the mutant.

On the other hand, when a raw carbon source such as cane molasses is used which contains more biotin than the proper amount for the growth of the mutant, an anti-biotin agent such as Penicillin, a higher fatty acid, or surface-active agent has to be added to the medium.

Cultivation is conducted under aerobic conditions for 20 to 80 hours at a temperature ranging from 30° to 38° C. The pH of the culture medium is controlled between 6.0 to 8.0 by the addition of an organic acid or inorganic acid, or alkali. For the purpose of pH adjustment, urea, $CaCO_3$ or gaseous ammonia is preferably used. L-glutamic acid accumulated in the culture broth can be

TABLE 2

| | | Degree of resistance to antibiotics | | | | |
|---|---|---|---|---|---|---|
| | Conc. | STRAIN NO. | | | | |
| Antibiotic | mg/ml | ATCC 13869 | AJ 11637 | AJ 11638 | ATCC 13032 | AJ 11645 |
| For. | 0 | 100 | 100 | | | |
| | 1 | 63 | 101 | | | |
| | 2 | 23 | 110 | | | |
| | 3 | 5 | 95 | | | |
| Cord. | 0 | 100 | 100 | | | |
| | 1 | 95 | 110 | | | |
| | 2 | 87 | 101 | | | |
| | 3 | 77 | 98 | | | |
| Tub. | 0 | 100 | 100 | | | |
| | 1 | 52 | 112 | | | |
| | 2 | 32 | 120 | | | |
| | 3 | 0 | 105 | | | |
| Dec. | 0 | 100 | | 100 | 100 | 100 |
| | 1 | 30 | | 109 | 61 | 115 |
| | 2 | 8 | | 103 | 5 | 102 |
| | 3 | 0 | | 82 | 0 | 89 |
| Psi. | 0 | 100 | | 100 | 100 | 100 |
| | 1 | 92 | | 105 | 99 | 107 |
| | 2 | 32 | | 110 | 23 | 95 |
| | 3 | 10 | | 84 | 0 | 78 | recovered by an entirely conventional recovery method.

The present invention can be further illustrated by the following Examples.

EXAMPLE 1

Twenty ml portions of an aqueous culture medium having the composition shown in Table 3 were poured into 500-ml flasks and heated at 115° C. for 10 minutes for sterilization.

TABLE 3

| Composition of culture medium | |
|---|---|
| Component | Conc. |
| Glucose | 36 mg/ml |
| Urea | 2 mg/ml |
| KH$_2$PO$_4$ | 1 mg/ml |
| MgSO$_4$ 7 H$_2$O | 0.4 mg/ml |
| FeSO$_4$ 7 H$_2$O | 10 μg/ml |
| MnSO$_4$ 4 H$_2$O | 8 μg/ml |
| Thiamine HC | 10 μg/ml |
| Biotin | 0.25 μg/ml |
| Soy protein hydrolyzed | 5 μl/ml |

Each test strain listed in Table 4 having grown on a bouillon agar medium, was inoculated into the medium and cultured at 31.5° C. with shaking. During the cultivation, a small amount of an aqueous solution containing 450 mg/ml urea was fed into the medium in order to maintain the pH of the culture medium in the range of 6.5 to 8.0. After 30 hours' cultivation, the amount of L-glutamic acid which accumulated in the culture broth was determined and the results obtained are shown in Table 4.

TABLE 4

| Strain No. | L-glutamic acid accumulated (g/l) | Yield (%) |
|---|---|---|
| ATCC 13869 | 16.3 | 45.3 |
| AJ 11637 | 16.7 | 46.4 |
| AJ 11638 | 16.9 | 46.9 |
| ATCC 13032 | 15.5 | 43.1 |
| AJ 11645 | 17.8 | 49.4 |

EXAMPLE 2

A culture medium containing, per milliliter, 100 mg sugar, (cane molasses), 1 mg KH$_2$PO$_4$, 1 μg thiamine, HCl, and 1 mg MgSO$_4$.7H$_2$O, and having a pH of 7.0, was prepared. Thirty ml portions of the medium were poured into 500 ml flasks and heated for sterilization. Then each test strain listed in Table 5 was inoculated into the medium and cultured at 31.5° C. with shaking. During the cultivation, a small amount of an aqueous solution of urea was fed into the medium in order to maintain the pH of the medium in the range from 6.5 to 8.0 and polyethylene sorbitan monopalmitate was added to the medium when the optical density at 26 times dilution of the culture medium came to 0.300.

After 36 hours' cultivation, the amount of L-glutamic acid which accumulated in the culture broth was determined and the results are shown in Table 5.

TABLE 5

| Strain No. | L-glutamic acid accumulated (g/l) | Yield (%) |
|---|---|---|
| ATCC 13869 | 49.3 | 49.3 |
| AJ 11637 | 50.1 | 50.1 |
| AJ 11638 | 49.5 | 49.5 |
| ATCC 13032 | 47.2 | 47.2 |
| AJ 11645 | 49.3 | 49.3 |

What is claimed is:

1. A method for producing L-glutamic acid by fermentation, which comprises: culturing aerobically in a culture medium a mutant of the genus of Brevibacterium or Corynebacterium which is resistant to Decoyinine, Psicofuranine, Formycin, Toyocamycin, Cordice, Sangwanycin, or Tubercidin and which is capable of producing L-glutamic acid, and recovering the L-glutamic acid which accumulates in the culture medium.

2. The method of claim 1, wherein said mutant belongs to the species Brevibacterium lactofermentum, Brevibacterium flavum, Corynebacterium glutamicum or Corynebacterium acetoacidophilum.

3. The method of claim 1, wherein said antibiotic is Decoyinine or Tubercidin.

* * * * *